United States Patent [19]

Juby

[11] 4,209,623

[45] Jun. 24, 1980

[54] PYRIMIDINE-5-N-(1H-TETRAZOL-5-yl-)-CARBOXAMIDES

[75] Inventor: Peter F. Juby, Jamesville, N.Y.

[73] Assignee: Bristol-Myers Company, New York, N.Y.

[21] Appl. No.: 913,277

[22] Filed: Jun. 7, 1978

[51] Int. Cl.$^2$ .................. A61K 31/505; C07D 403/12
[52] U.S. Cl. .................................... 544/319; 424/251; 546/210; 548/343
[58] Field of Search .......................................... 544/319

[56] References Cited

U.S. PATENT DOCUMENTS

| | | | |
|---|---|---|---|
| 3,448,107 | 6/1969 | Holland | 260/250 |
| 3,660,403 | 5/1972 | Shen | 260/251 R |
| 3,745,161 | 7/1973 | Shen | 260/250 R |
| 3,883,653 | 5/1975 | Barth | 424/251 |
| 4,031,093 | 6/1977 | Juby | 260/251 R |
| 4,082,751 | 4/1978 | Juby | 260/256.4 C |

OTHER PUBLICATIONS

Ruhemann, S., Ber., 30, 821, (1897).
Mitter et al., "J. Chem. Soc.", 123, 2179, (1923).
Mitter et al., "Quart J. Indian. Chem. Soc.", 2, p. 61, (1925).

Primary Examiner—Donald G. Daus
Assistant Examiner—Lisa Jones
Attorney, Agent, or Firm—David M. Morse

[57] ABSTRACT

A series of 1,6-dihydro-6-oxo-2-phenylpyrimidine-5-N-(1H-tetrazol-5-yl)carboxamides is provided for use as inhibitors of allergic reactions. The compounds show antiallergy activity by both oral and parenteral routes of administration.

27 Claims, No Drawings

PYRIMIDINE-5-N-(1H-TETRAZOL-5-YL)-CARBOXAMIDES

BACKGROUND OF THE INVENTION

1. Field of the Invention:

This invention relates to optionally substituted 1,6-dihydro-6-oxo-2-phenylpyrimidine-5-N-(1H-tetrazol-5-yl)-carboxamide derivatives and to their use as inhibitors of allergic reactions.

2. Description of the Prior Art:

Various medicinal agents have been employed in the treatment of allergic reactions such as bronchial asthma and allergic rhinitis which are believed to result mainly from antigenantibody interaction. With respect to bronchial asthma, one of the most serious of these allergically-mediated diseases, bronchodilators such as theophylline, isoproterenol, epinephrine and atropine are used primarily in providing symptomatic relief. These agents, however, have undesirable side effects, e.g. cardiac stimulation and gastrointestinal distress.

With the recent introduction of disodium cromoglycate described by J. S. G. Cox, et al. in *Adv. in Drug Res.*, 5, 115–196 (1970), the physician has been provided with an agent which, when administered to asthmatic patients prior to inhalation of specific antigens, inhibits the release of mediators, e.g. histamine and SRS-A (slow-reacting-substance of anaphylaxis), believed to be responsible for the asthmatic response. While making possible a prophylactic treatment for bronchial asthma without cardiovascular side effects and thus representing a significant advance, disodium cromoglycate suffers from a major disadvantage in that it is not orally absorbed and must be administered by inhalation.

With respect to the compounds of the present invention, no examples of 1,6-dihydro-6-oxo-2-phenylpyrimidine-5-N-(1H-tetrazol-5-yl)carboxamides have been found in the literature. Numerous examples of 1,6-dihydro-6-oxo-2-phenylpyrimidine-5-carboxylic acid derivatives are known, however. Illustrative of such compounds are the following:

1. Preparation of the unsubstituted acid and ester of the formula

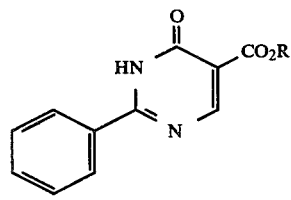

where R is hydrogen or ethyl is disclosed by S. Ruhemann in *Ber.*, 30, 821 (1897).

2. The p-methylphenyl and p-methoxyphenyl substituted esters and acids of the formula

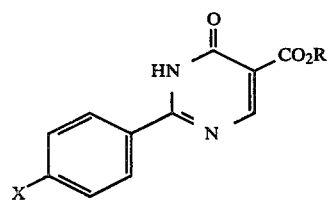

where R is hydrogen or ethyl and X is methyl or methoxy are disclosed by Mitter, et al. in *J. Chem. Soc.*, 123, 2179 (1923) and *Quart. J. Indian Chem. Soc.*, 2, 61 (1925).

3. Shen, et al. in U.S. Pat. Nos. 3,660,403 and 3,745,161 disclose compounds of the general formula

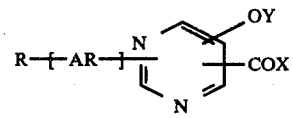

where R—[Ar]— may inter alia be substituted phenyl, Y may be hydrogen and X is any of various substituents including hydroxy, alkoxy or N-heterocyclo. The reference compounds are disclosed as having antiinflammatory, antipyretic and analgesic activity, and no mention is made of any utility as antiallergy agents.

4. U.S. Pat. No. 3,883,653 discloses antiallergy compounds of the formula

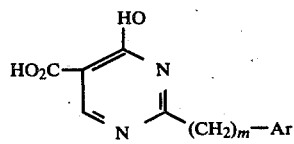

where m is an integer of 0 or 1 and Ar is pyridyl, thienyl, furyl, phenyl or phenyl substituted by hydroxy, methyl, methoxy, nitro, chloro, fluoro, 3,4-dimethoxy, 3,4,5-trimethoxy or alkanoylamino.

5. U.S. Pat. No. 3,448,107 discloses lipid regulating agents of the formula

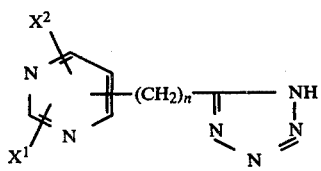

where $X^1$ and $X^2$ may be various substituents including hydroxy, phenyl, p-chlorophenyl, p-methylphenyl and p-aminophenyl and n may be 0 to 4.

6. U.S. Pat. No. 4,031,093 discloses 1,6-dihydro-6-oxo-2(ortho-substituted phenyl)pyrimidine-5-carboxylic acid derivatives of the formula

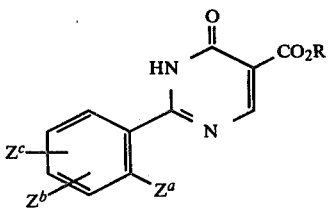

wherein $Z^a$ is —O—$C_1$—$C_6$ alkyl, —O—$C_2$—$C_6$ alkenyl, —O—$(CH_2)_m$—CH$(CH_2)_n$ in which m is 0 or an integer from 1 to 6 and n is an integer from 2 to 7, —OCH$_2$(CH$_2$)$_x$O(CH$_2$)$_y$CH$_3$ in which x and y are each independently either 0 or an integer from 1 to 6, —OCF$_3$, —OCH$_2$CF$_3$, —O(CH$_2$)$_u$CO$_2$R$^a$ in which u is an integer from 1 to 6 and R$^a$ is hydrogen or C$_1$-C$_6$ alkyl, R$^c$—COO— in which R$^c$ is C$_1$-C$_6$ alkyl, —O—CONHR$^b$ in which R$^b$ is C$_1$-C$_6$ alkyl, —O(CH$_2$)$_k$OH in which k is an integer from 2 to 6,

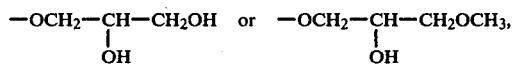

Z$^b$ has the meaning stated above for Z$^a$ and in addition may be hydrogen, halogen, amino, C$_1$-C$_6$ alkylamino, di(C$_1$-C$_6$)-alkylamino, —N(CH$_2$)$_r$ in which r is 4 or 5,

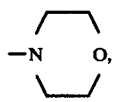

carb(C$_1$-C$_6$)alkoxy, C$_1$-C$_6$ alkyl, C$_2$-C$_6$ alkenyl, CF$_3$, hydroxy, C$_1$-C$_6$ alkylthio, R$^c$—CO— in which R$^c$ is C$_1$-C$_6$ alkyl or R$^c$—CONH— in which R$^c$ is C$_1$-C$_6$ alkyl, Z$^c$ is hydrogen or C$_1$-C$_6$ alkoxy and R is hydrogen or the residue of an easily cleavable ester group or a pharmaceutically acceptable salt thereof, provided that when Z$^a$ is methoxy, Z$^b$ and Z$^c$ are not hydrogen and when Z$^c$ is C$_1$-C$_6$ alkoxy, Z$^a$ and Z$^b$ are both C$_1$-C$_6$ alkoxy.

7. U.S. Pat. No. 4,082,751 discloses 2-phenyl-5-(5-1H-tetrazolyl)pyrimidin-4(3H)-one derivatives of the formula

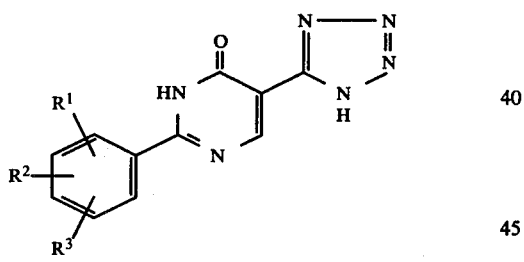

wherein R$^1$, R$^2$ and R$^3$ which may be the same or different are each hydrogen, halogen, (lower)alkyl, (lower)alkenyl, (lower)alkoxy, —O—(CH$_2$-)$_m$—CH(CH$_2$)$_n$ in which m is 0 or an integer from 1 to 6 and n is an integer from 2 to 7, —OCH$_2$(CH$_2$)$_x$O(CH$_2$)$_y$CH$_3$ in which x is 0 or an integer from 1 to 6 and y is 0 or an integer from 1 to 6, CF$_3$, —OCF$_3$, —OCH$_2$CF$_3$, hydroxy, (lower)alkylthio, amino, nitro, —N(CH$_2$)$_r$ in which r is 4 or 5,

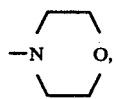

(lower)alkylamino, di(lower)alkylamino, carboxyl, —CO$_2$—(lower)alkyl, —O(CH$_2$)$_u$CO$_2$R$^a$ in which u is an integer from 1 to 6 and R$^a$ is hydrogen or (lower)alkyl, acyl, acylamino, acyloxy, $$-O-\overset{\overset{O}{\|}}{C}-NHR^b$$

in which R$^b$ is (lower)alkyl, —O(CH$_2$)$_k$OH in which k is an integer from 2 to 6,

—OCH$_2$—CH(OH)—CH$_2$OH,

—OCH$_2$—CH(OH)—CH$_2$OCH$_3$ or —OCH$_2$C$_6$H$_5$, and pharmaceutically acceptable salts thereof, with the proviso that R$^1$, R$^2$ and R$^3$ may not all be alike except in the case where they represent (lower)alkoxy.

SUMMARY OF THE INVENTION

This invention relates to new therapeutically useful 1,6-dihydro-6-oxo-2-phenylpyrimidine-5-N-(1H-tetrazol-5-yl)-carboxamide derivatives, to processes for their preparation, to pharmaceutical compositions containing them and to methods for treating allergically-mediated diseases in mammals by administration of such derivatives or pharmaceutical compositions.

The compounds of the present invention are useful in the prophylactic treatment of allergic conditions such as bronchial asthma, allergic rhinitis, urticaria, systemic anaphylaxis, conjunctivitis, atopic dermatitis and food allergies. They are of particular value in both reagin-mediated type I hypersensitivity asthma (extrinsic asthma) and the so-called intrinsic asthma in which no sensitivity to any extrinsic antigen can be demonstrated.

The antiallergy agents of the present invention may be represented by the formula

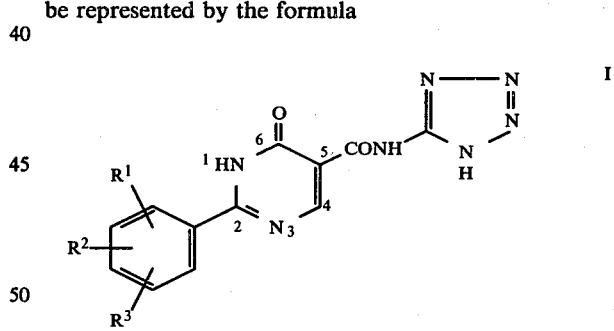

wherein R$^1$, R$^2$ and R$^3$ which may be the same or different are each hydrogen, halogen, (lower)alkyl, (lower)alkenyl, (lower)-alkoxy, —O—(lower)alkenyl, —O—(lower)alkynyl, —O—(CH$_2$)$_m$—CH(CH$_2$)$_n$ in which m is 0 or an integer from 1 to 6 and n is an integer from 2 to 7, —OCH$_2$(CH$_2$)$_x$O(CH$_2$)$_y$CH$_3$ in which x is 0 or an integer from 1 to 6 and y is 0 or an integer from 1 to 6, CF$_3$, —OCF$_3$, —OCH$_2$CF$_3$, hydroxy, (lower)alkylthio, amino, nitro, —N(CH$_2$)$_r$ in which r is 4 or 5, (lower)alkylamino, di(lower)alkylamino, carboxyl, —CO$_2$—(lower)alkyl, —O(CH$_2$)$_u$CO$_2$R$^a$ in which u is an integer from 1 to 6 and R$^a$ is hydrogen or (lower)alkyl, R$^c$—CO— in which R$^c$ is (lower)alkyl, R$^c$—CONH— in which R$^c$ is (lower)alkyl, R$^c$—COO— in which R$^c$ is (lower)alkyl,

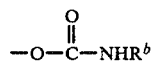

in which $R^b$ is (lower)alkyl, $-O(CH_2)_kOH$ in which k is an integer from 2 to 6,

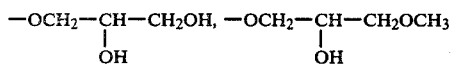

or $-OCH_2C_6H_5$, or a pharmaceutically acceptable salt thereof, with the provisos that (1) no more than two of $R^1$, $R^2$ and $R^3$ are tertiary alkyl or tertiary alkoxy groups, and when two of said $R^1$, $R^2$ and $R^3$ are tertiary alkyl or tertiary alkoxy, they are located on non-adjacent positions and (2) $R^1$, $R^2$ and $R^3$ may not all be alike except in the case where they represent hydrogen or (lower)alkoxy.

DETAILED DESCRIPTION

The $R^1$, $R^2$ and $R^3$ substituents mentioned above may be located at any of the available positions of the phenyl ring, i.e. at the 2–6 positions. The substituents groups may be further defined as follows:

(a) Halogen includes chlorine, bromine, fluorine and iodine;

(b) (Lower)alkyl includes both straight and branched chain saturated aliphatic hydrocarbon radicals having from 1–6 carbon atoms inclusive, e.g. methyl, ethyl, n-propyl, isopropyl, n-butyl, isobutyl, sec-butyl, tert-butyl, n-pentyl, isopentyl, n-hexyl, etc.;

(c) (Lower)alkenyl includes straight or branched unsaturated aliphatic hydrocarbon radicals containing one double bond and having from 2–6 carbon atoms inclusive, e.g. vinyl, allyl, isopropenyl, 2- or 3-methallyl or 3-butenyl;

(d) (Lower)alkoxy includes $C_1$–$C_6$ alkoxy radicals, the alkyl portion of such radicals being defined as in (b) above. Examples include methoxy, ethoxy, n-propoxy, isopropoxy, n-butoxy, isobutoxy, sec-butoxy, n-pentyloxy, isopentyloxy, n-hexyloxy, etc.;

(e) —O—(Lower)alkenyl groups include radicals in which the alkenyl portion is as defined above in (c), e.g. vinyloxy, allyloxy or isopropenyloxy;

(f) $-O-(CH_2)_m-CH(CH_2)_n$ includes cyclo(lower)alkyloxy and cyclo(lower)alkyl-$(C_1-C_6)$alkyloxy groups in which the cycloalkyl ring contains from 3 to 8 carbon atoms, preferably 3–6 carbon atoms. Examples of such groups are cyclopropyloxy, cyclobutyloxy, cyclopentyloxy, cyclohexyloxy, cycloheptyloxy, cyclopropylmethyloxy, cyclopropylethyloxy, cyclobutylmethyloxy, cyclobutylethyloxy, cyclopentylmethyloxy, cyclohexylmethyloxy, cyclohexylethyloxy and cyclohexylpropyloxy;

(g) $-O-CH_2(CH_2)_xO(CH_2)_yCH_3$ includes radicals such as $-OCH_2OCH_3$, $-OCH_2CH_2OCH_3$, $-OCH_2CH_2OCH_2CH_3$, $-OCH_2OCH_2CH_3$ and $-OCH_2CH_2CH_2OCH_2CH_3$;

(h) (lower)alkylthio includes $C_1$–$C_6$ alkylthio radicals in which the alkyl portion is as defined above in (b). Examples of such groups are methylthio, ethylthio, n-propylthio and n-butylthio;

(i) (Lower)alkylamino includes $C_1$–$C_6$ alkylamino radicals in which alkyl is as defined in (b). Examples of such groups as methylamino, ethylamino, propylamino and butylamino;

(j) Di(lower)alkylamino includes di $C_1$–$C_6$ alkylamino radicals in which alkyl is as defined above in (b). Examples of such groups are dimethylamino and diethylamino;

(k) —CO—(Lower)alkyl includes ester radicals in which the alkyl moiety is as defined above in (b), e.g. carbomethoxy, carbethoxy, carbopropoxy and carbobutoxy;

(l) $-O(CH_2)_uCO_2R^a$ represents radicals such as $-OCH_2CO_2H$, $-OCH_2CH_2CO_2H$, $-OCH_2CH_2CH_2CO_2H$, $-OCH_2CO_2CH_3$, $-OCH_2CO_2C_2H_5$, $-OCH_2CH_2CO_2CH_3$ and $-OCH_2CH_2CO_2C_2H_5$;

(m) $-N(CH_2)_r$ includes pyrrolidino and piperidino;

(n)

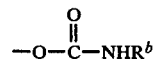

includes (lower)alkyl carbamoyloxy radicals in which the (lower)alkyl portion is as defined above in (b). Examples of such substituents include $-OCONHCH_3$, $-OCONHC_2H_5$ and $-OCONHC_3H_7$; and (o) —O—(Lower)alkynyl includes groups in which the alkynyl moiety is a straight or branched unsaturated aliphatic hydrocarbon radical containing one triple bond and having from 2 to 6 carbon atoms inclusive, e.g. ethynyloxy, propargyloxy, butynyloxy, pentynyloxy or hexynyloxy.

A preferred embodiment of the present invention comprises the compounds of formula I as defined above wherein $R^1$, $R^2$ and $R^3$ are each independently selected from hydrogen, (lower)alkoxy, —O—(lower)alkenyl, —O—(lower)-alkynyl, $-O-(CH_2)_m-CH(CH_2)_n$ in which m is 0 or an integer from 1 to 6 and n is an integer from 2 to 7, $-OCH_2C_6H_5$, halogen, $CF_3$, (lower)alkyl, amino, (lower)alkylamino, di(lower)alkylamino, hydroxy, carboxy and (lower)alkylthio. Within this group of compounds, a more preferred embodiment comprises those compounds wherein $R^1$, $R^2$ and $R^3$ are each independently selected from hydrogen, (lower)alkoxy, —O—(lower)alkenyl, —O—(lower)alkynyl, $-O-(CH_2)_m-CH(CH_2)_n$ in which m is 0 or an integer from 1 to 6 and n is an integer from 2 to 7 and $-OCH_2C_6H_5$.

A more preferred embodiment of the present invention comprises the compounds of the formula

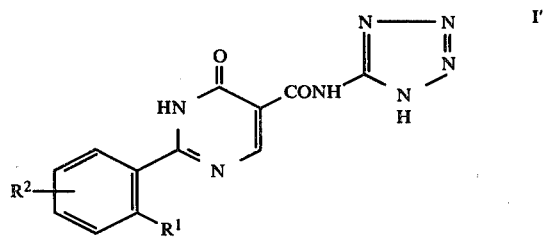

wherein $R^1$ and $R^2$ which may be the same or different are as defined above in connection with the compounds of general formula I, and the pharmaceutically acceptable salts thereof, with the proviso that when both $R^1$ and $R^2$ are tertiary alkyl or tertiary alkoxy groups, they are located on non-adjacent positions.

A preferred subgroup within the compounds defined by formula I' comprises the compounds wherein R¹ and R² are each independently selected from hydrogen, (lower)alkoxy, —O—(lower)alkenyl, —O—(lower)alkynyl, —O—(CH₂)$_m$—CH(CH₂)$_n$ in which m is 0 or an integer from 1 to 6 and n is an integer from 2 to 7, —OCH₂C₆H₅, halogen, CF₃, (lower)alkyl, amino, (lower)alkylamino, di(lower)alkylamino, hydroxy, carboxy and (lower)alkylthio. Within this subgroup, the preferred compounds are those in which R¹ and R² are each independently selected from hydrogen, (lower)alkoxy, —O—(lower)alkenyl, —O—(lower)alkynyl, —O—(CH₂)$_m$—CH(CH₂)$_n$ in which m is 0 or an integer from 1 to 6 and n is an integer from 2 to 7 and —OCH₂C₆H₅. The most preferred compounds within this latter group are those in which R¹ is a non-hydrogen substituent.

A most preferred subgroup within the compounds defined by formula I' comprises the compounds wherein R¹ is (lower)alkoxy, —O—(lower)alkenyl, —O—(lower)alkynyl, —O—(CH₂)$_m$—CH(CH₂)$_n$ in which m is 0 or an integer from 1 to 6 and n is an integer from 2 to 7 or —OCH₂C₆H₅ and R² is hydrogen, (lower)alkoxy, —O—(lower)alkenyl, —O—(lower)alkynyl, —O—(CH₂)$_m$—CH(CH₂)$_n$ in which m is 0 or an integer from 1 to 6 and n is an integer from 2 to 7, —OCH₂C₆H₅, amino, di(lower)alkylamino or (lower)alkylthio.

Another more preferred embodiment of the present invention comprises the compounds of the formula

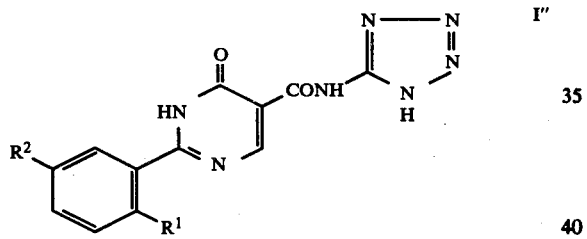

wherein R¹ and R² which may be the same or different are as defined above in connection with the compounds of general formula I, and the pharmaceutically acceptable salts thereof.

A preferred subgroup within the compounds defined by formula I" comprises the compounds wherein R¹ and R² are each independently selected from hydrogen, (lower)-alkoxy, —O—(lower)alkenyl, —O—(lower)alkynyl, —O—(CH₂)$_m$—CH(CH₂)$_n$ in which m is 0 or an integer from 1 to 6 and n is an integer from 2 to 7, —OCH₂C₆H₅, halogen, CF₃, (lower)alkyl, amino, (lower)alkylamino, di(lower)alkylamino, hydroxy, carboxy and (lower)alkylthio. Within this subgroup, the preferred compounds are those in which R¹ and R² are each independently selected from hydrogen, (lower)alkoxy, —O—(lower)alkenyl, —O—(lower)alkynyl, —O—(CH₂)$_m$—CH(CH₂)$_n$ in which m is 0 or an integer from 1 to 6 and n is an integer from 2 to 7 and —OCH₂C₆H₅. The most preferred compounds within this latter group are those in which R¹ is a nonhydrogen substituent.

A most preferred subgroup within the compounds defined by formula I" comprises the compounds wherein R¹ is (lower)alkoxy, —O—(lower)alkenyl, —O—(lower)alkynyl, —O—(CH₂)$_m$—CH(CH₂)$_n$ in which m is 0 or an integer from 1 to 6 and n is an integer from 2 to 7 or —OCH₂C₆H₅ and R² is hydrogen, (lower)alkoxy, —O—(lower)alkenyl, —O—(lower)alkynyl, —O—(CH₂)$_m$—CH(CH₂)$_n$ in which m is 0 or an integer from 1 to 6 and n is an integer from 2 to 7, —OCH₂C₆H₅, amino, di(lower)alkylamino or (lower)alkylthio.

Other most preferred subgroups within the compounds defined by formula I" are as follows:

(a) compounds where R¹ is (lower)alkoxy, most preferably methoxy, ethoxy, n-propoxy, isopropoxy, n-butoxy, isobutoxy, sec-butoxy or t-butoxy;
(b) compounds where R¹ is —O—(lower)alkenyl, most preferably allyloxy;
(c) compounds where R¹ is —O—(CH₂)$_m$—CH(CH₂)$_n$ in which m is 0 or an integer from 1 to 6 and n is an integer from 2 to 7, most preferably cyclopropylmethoxy; and
(d) compounds where R¹ is methoxy, ethoxy, n-propoxy, isopropoxy, n-butoxy, isobutoxy, sec-butoxy, t-butoxy, allyloxy or cyclopropylmethoxy and R² is methoxy, ethoxy, n-propoxy, isopropoxy, n-butoxy, isobutoxy, sec-butoxy, t-butoxy, allyloxy, cyclopropylmethoxy, amino or dimethylamino.

Another more preferred embodiment of the present invention comprises the compounds of the formula

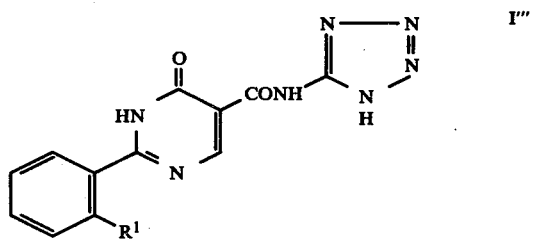

wherein R¹ is hydrogen, halogen, (lower)alkyl, (lower)-alkenyl, (lower)alkoxy, —O—(lower)alkenyl, —O—(lower)-alkynyl, —O—(CH₂)$_m$—CH(CH₂)$_n$ in which m is 0 or an integer from 1 to 6 and n is an integer from 2 to 7, —OCH₂(CH₂)$_x$O(CH₂)$_y$CH₃ in which x is 0 or an integer from 1 to 6 and y is 0 or an integer from 1 to 6, CF₃, —OCF₃, —OCH₂CF₃, hydroxy, (lower)alkylthio, amino, nitro, —N(CH₂)$_r$ in which r is 4 or 5, (lower)alkylamino, di(lower)alkylamino, carboxyl, —CO₂—(lower)alkyl, —O(CH₂)$_u$CO₂R$^a$ in which u is an integer from 1 to 6 and R$^a$ is hydrogen or (lower)alkyl, R$^c$—CO— in which R$^c$ is (lower)alkyl, R$^c$—CONH— in which R$^c$ is (lower)-alkyl, R$^c$—COO— in which R$^c$ is (lower)alkyl,

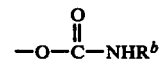

in which R$^b$ is (lower)alkyl, —O(CH₂)$_k$OH in which k is an integer from 2 to 6,

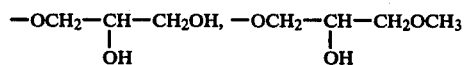

or —OCH₂C₆H₅, or a pharmaceutically acceptable salt thereof.

A preferred subgroup within the compounds defined by formula I'" comprises the compounds wherein R¹ is hydrogen, (lower)alkoxy, —O—(lower)alkenyl, —O—(lower)-alkynyl, —O—(CH$_2$)$_m$—CH(CH$_2$)$_n$ in which m is 0 or an integer from 1 to 6 and n is an integer from 2 to 7, —OCH$_2$C$_6$H$_5$, halogen, CF$_3$, (lower)alkyl, amino, (lower)alkylamino, di(lower)alkylamino, hydroxy, carboxy or (lower)alkylthio. Within this subgroup, the preferred compounds are those in which R$^1$ is (lower)alkoxy, —O—(lower)alkenyl, —O—(lower)-alkynyl, —O—(CH$_2$)$_m$—CH(CH$_2$)$_n$ in which m is 0 or an integer from 1 to 6 and n is an integer from 2 to 7 or —OCH$_2$C$_6$H$_5$.

Other preferred subgroups within the compounds defined by formula I''' are as follows:

(a) compounds where R$^1$ is (lower)alkoxy, most preferably methoxy, ethoxy, n-propoxy, isopropoxy, n-butoxy, isobutoxy, sec-butoxy or t-butoxy;

(b) compounds where R$^1$ is —O—(lower)alkenyl, most preferably allyloxy;

(c) compounds where R$^1$ is —O—(CH$_2$)$_m$—CH(CH$_2$)$_n$ in which m is 0 or an integer from 1 to 6 and n is an integer from 2 to 7, most preferably cyclopropylmethoxy;

(d) compounds where R$^1$ is —O—(lower)alkynyl; and (e) compounds where R$^1$ is —OCH$_2$C$_6$H$_5$.

The term "pharmaceutically acceptable salt" as used herein is intended to include non-toxic cationic salts such as the alkali metal salts, e.g. sodium and potassium, alkaline earth metal salts such as calcium, magnesium or barium, aluminum salts, ammonium salts, and salts with organic bases, e.g. amines such as triethylamine, n-propylamine, tri-n-butylamine, piperidine, ethanolamine, diethanolamine, triethanolamine, diethylaminoethylamine, ethylenediamine, N,N'-dibenzylethylenediamine, benzylamine, tris(hydroxymethyl)aminomethane or pyrrolidine. Salt formation is accomplished by reacting the appropriate pyrimidine-5-N-(1H-tetrazol-5-yl)carboxamide with a substantially equimolar amount of the appropriate base in an aqueous solution or in a suitable organic solvent such as methanol or ethanol. The salts are recovered by standard methods such as filtration if they are insoluble in the reaction medium, or if they are soluble in the medium, by evaporation or by precipitation by addition of a non-solvent for the salt.

Those skilled in the art will appreciate that the compounds represented by structural formulae I-I''' are capable of also existing in the tautomeric forms shown below. All of the forms may be present to a greater or lesser degree and may co-exist in a dynamic equilibrium mixture. While all of the various tautomeric forms are included within the scope of the present invention, the form represented by formula 1 below has been arbitrarily used herein for the sake of convenience to describe the present compounds.

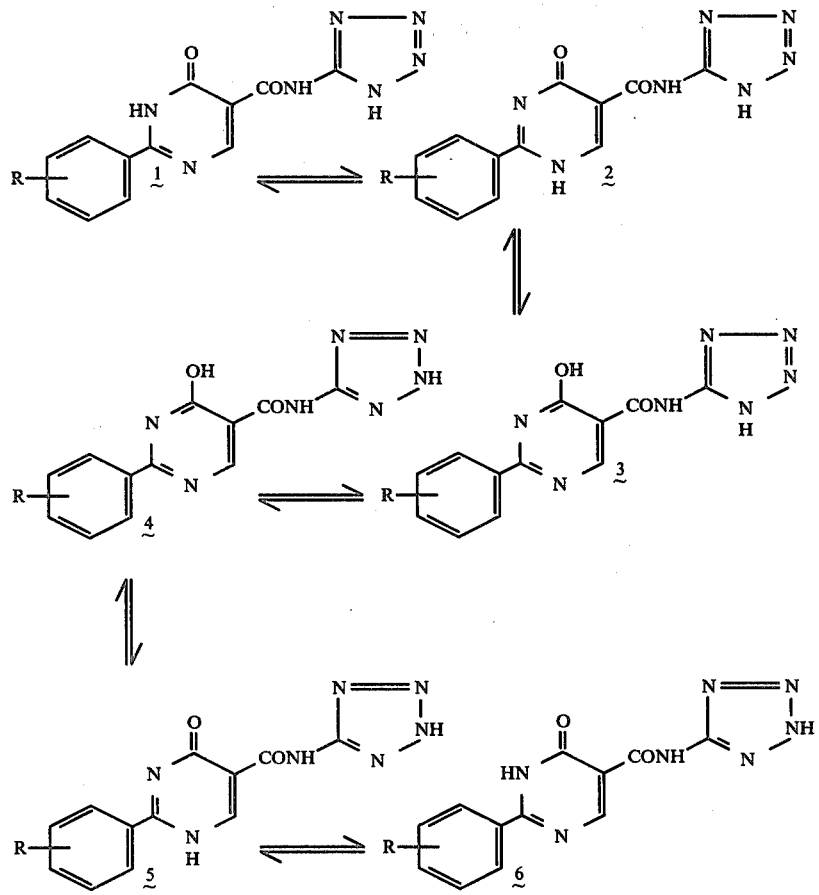

The compounds of formula I may be prepared by coupling of the appropriate pyrimidine-5-carboxylic acid of the formula

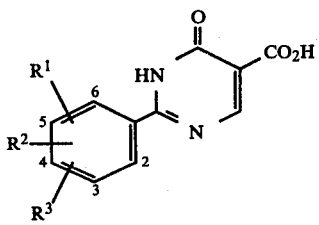

wherein $R^1$, $R^2$ and $R^3$ are as defined above with 5-aminotetrazole of the formula

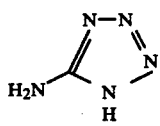

The coupling of the acid II with the amino-tetrazole III may be accomplished with the aid of a variety of reagents commonly used, for example, in peptide synthesis. Examples of these reagents are described by Schröder and Lübke in "The Peptides", Vol. I, Academic Press, N.Y., 1965, pp. 77–128. The general principle of the synthesis is activation of the carboxyl group by either formation, for example, of the corresponding acid azide, acid halide (preferably the acid chloride), mixed anhydride (e.g. with carbonic acid monoesters), activated ester (e.g. p-nitrophenyl), or heterocyclic amide (e.g. imidazolide), or by treatment with a carbodiimide (e.g. N,N'-dicyclohexylcarbodiimide). Treatment of the activated carboxyl group with 5-aminotetrazole results in amide formation. The coupling reaction is carried out in a reaction-inert solvent system. The variety of coupling reagents which can be used allows a wide choice of solvents. Representative solvents are N,N-dimethylformamide, tetrahydrofuran, dioxane, methylene chloride, nitromethane, acetonitrile, dimethylsulfoxide, N,N-dimethylacetamide and hexamethylphosphoramide. Reaction times and temperatures are not critical. For good yields of products within a reasonable length of time, convenient temperatures are in the range of about 20°–100° C. for both steps, i.e. reaction of the acid with the coupling agent the reaction of the activated intermediate with the 5-aminotetrazole. The coupling reaction may be carried out either in stepwise fashion, i.e. by isolating the activated intermediate before addition of the 5-aminotetrazole, or by adding all reactants at once.

A preferred method of coupling utilizes N,N'-carbonyldiimidazole and is illustrated by the following scheme:

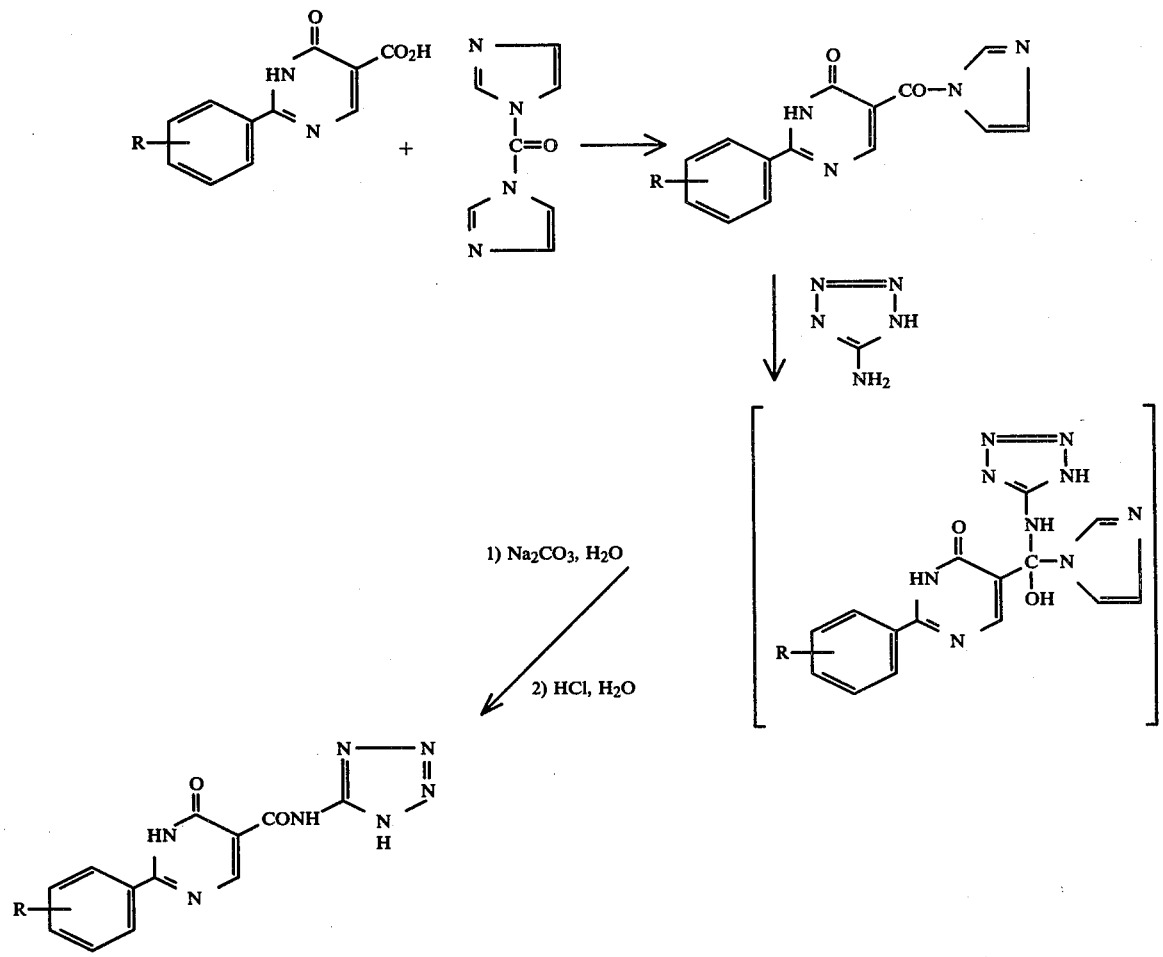

This reaction scheme may be carried out using the reaction-inert solvents mentioned above in both the imidazolide formation step and the step in which the imidazolide (either in situ or isolated) is reacted with the aminotetrazole. Preferred solvents are tetrahydrofuran and N,N-dimethylformamide. The reaction temperature is not critical, but a convenient temperature range for both steps has been found to be about 20°–100° C.

The pyrimidine-5-carboxylic acids of formula II may be prepared as described in U.S. Pat. No. 4,031,093 or by hydrolysis of the pyrimidine-5-carboxylate esters disclosed in U.S. Pat. No. 4,082,751. The 5-aminotetrazole starting material is commercially available.

In preparing compounds of formula I which contain free hydroxy, amino or carboxyl groups, it is of course understood that such groups will be protected by conventional protecting groups during the coupling reaction of II with III. The protecting group(s) may then be removed by methods known per se to give the desired end-products having the unprotected substituent groups. Amino-substituted compounds may be prepared from the corresponding nitro-substituted product by catalytic hydrogenation. In preparing compounds of formula I where $R^1$, $R^2$ or $R^3$ are (lower)alkylamino or di(lower)alkylamino, the corresponding amino-substituted compound may first be prepared and then alkylated. Alternatively, the dialkylamino-substituted compounds can be prepared directly from the appropriate starting material of formula II.

In another aspect, the present invention provides a method of inhibiting or preventing the symptoms of an allergic reaction such as bronchial asthma, allergic rhinitis, urticaria, allergic conjunctivitis, systemic anaphylaxis, atopic dermatitis and food allergy in a mammal susceptible to such a reaction which comprises administering to said mammal a prophylactically effective dose of a compound of formula I or a pharmaceutically acceptable salt thereof.

The compounds of the present invention may be administered either as individual therapeutic agents or as mixtures with other therapeutic agents. They may be administered alone but are generally administered in the form of pharmaceutical compositions, i.e. mixtures of the active agents with suitable pharmaceutical carriers or diluents. Examples of such compositions include tablets, lozenges, capsules, powders, aerosol sprays, aqueous or oily suspensions, syrups, elixirs and aqueous solutions. The compounds are preferably administered orally, but may also be administered by inhalation, injection, instillation or by implantation for controlled drug release from a solid carrier reservoir.

The nature of the pharmaceutical composition and the pharmaceutical carrier or diluent will, of course, depend on the desired route of administration. For example, oral compositions may be in the form of tablets or capsules and may contain conventional excipients such as binding agents (e.g. syrup, acacia, gelatin, sorbitol, tragacanth or polyvinylpyrrolidone), fillers (e.g. lactose, sugar, maize-starch, calcium phosphate, sorbitol or glycine), lubricants (e.g. magnesium stearate, talc, polyethylene glycol, or silica), disintegrants (e.g. starch) or wetting agents (e.g. sodium lauryl sulfate). Oral liquid preparations may be in the form of aqueous or oily suspensions, solutions, emulsions, syrups, elixirs, etc. or may be presented as a dry product for reconstitution with water or other suitable vehicle before use. Such liquid preparations may contain conventional additives such as suspending agents, flavoring agents, diluents or emulsifying agents. For parenteral administration, inhalation or instillation, solutions or suspensions of a compound of formula I with conventional pharmaceutical vehicles may be employed, e.g. as an aerosol spray for inhalation, as an aqueous solution for intravenous injection or instillation, or as an oily suspension for intramuscular injection. The compounds may also be administered by means of inhalers or other devices which permit the active compounds in the form of dry powders to come into direct contact with the lungs.

The compounds of the present invention or pharmaceutical compositions thereof may be administered to human allergic patients in single oral doses of approximately 0.5—500 mg. of active ingredient and multiple oral doses totalling up to about 1000 mg./day of active ingredient. When administered by inhalation or instillation, lower doses are generally given, i.e. on the order of about 0.1 of the normal oral dosage for the particular compound in question. These values are illustrative only, however, and the physician of course will ultimately determine the dosage most suitable for a particular patient on the basis of factors such as age, weight, severity of the symptoms and the particular agent to be administered.

The in vivo animal model studies described below indicate that the compounds of formula I are highly potent antiallergy agents.

BIOLOGICAL ACTIVITY DATA

The reagin-mediated rat Passive Cutaneous Anaphylaxis (PCA) screening test used to evaluate the present compounds is generally regarded as one of the best animal models for use in predicting the antiallergy activity of test compounds in man. This screen provides a measure of the effectiveness of test compounds in either inhibiting the release or antagonizing the action of mediators arising from the interaction of reaginic antibodies with specific antigen, mediators which are causative factors in allergic disorders. The details of the test are fully described in U.S. Pat. No. 4,031,093.

The test compounds were solubilized in aqueous sodium bicarbonate and administered intravenously (i.v.) or per os (p.o.) either one or ten minutes, respectively, prior to antigen callenge. Disodium cromoglycate (DSCG), solubilized in saline, was administered i.v. at the time of challenge and p.o. 30 minutes prior to challenge. Test results were recorded in terms of the $ID_{50}$ value, i.e. the dose of compound that inhibits 50% of the response. To illustrate the relative potency of the present compounds, the compound of Example 1 in the rat PCA test was found to have an $ID_{50}$ of ~0.051 mg./kg. (i.v.) and ~0.56 mg./kg. (p.o.) as compared to 0.6 mg./kg. (i.v.) and >>30 mg./kg. (p.o.) for DSCG.

The following examples are provided solely for the purpose of illustrating preparation of the compounds of the present invention and are not to be construed as limitations of the invention. All temperatures referred to below are in degrees Celsius. The compounds shown below in Examples 1 and 2 have the general structural formula

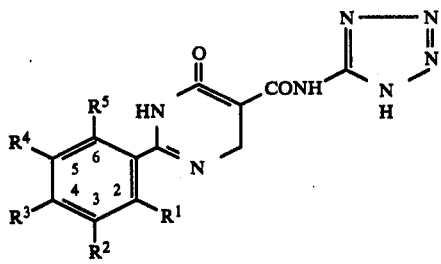

EXAMPLE 1

1,6-Dihydro-6-oxo-2-(2-ethoxyphenyl)pyrimidine-5-N-(1H-tetrazol-5-yl)carboxamide ($R^1=C_2H_5O—$; $R^2$, $R^3$, $R^4$, $R^5=H$)

A slurry of N,N'-carbonyldiimidazole (3.24 g., 0.02 mole) in tetrahydrofuran (20 ml.) was added to a stirred suspension of 1,6-dihydro-6-oxo-2-(2-ethoxyphenyl)-pyrimidine-5-carboxylic acid (2.60 g., 0.01 mole) in tetrahydrofuran (40 ml.). The mixture was stirred under reflux for 16 hours. The solvent was removed. A mixture of the residual solid and 5-aminotetrazole (1.03 g., 0.012 mole) in tetrahydrofuran (40 ml.) was heated under reflux for 2 hours. The cooled mixture was filtered, and the collected material (3.3 g.) recrystallized from N,N-dimethylformamide to give a white solid, m.p. 228°–230° (decomp). A portion (1.0 g.) of the solid was dissolved in 5% aqueous sodium carbonate. The solution was treated with 6 N hyrochloric acid acid to pH 2. The mixture was filtered and the collected solid washed with water followed by acetone. A slurry of the solid in water (15 ml.) was treated with a few drops of 6 N hydrochloric acid, and the mixture stirred vigorously for 15 minutes. The white solid was collected by filtration, washed with water followed by acetone, and dried to give the title compound, m.p. 284°–285°.

Anal. Calcd for $C_{14}H_{13}N_7O_3$: C, 51.37; H, 4.00; N, 29.96. Found: C, 50.81; H, 4.02; N, 30.00.

EXAMPLE 2

If in the procedure of Example 1 the 1,6-dihydro-6-oxo-2-(2-ethoxyphenyl)pyrimidine-5-carboxylic acid is replaced by an equimolar weight of the pyrimidine-5-carboxylic acids listed in Table A below, there are produced the carboxamide products listed in Table B.

| Table A | Table B |
| --- | --- |
| 1,6-dihydro-6-oxo-2-(2-n-propoxyphenyl)pyrimidine-5-carboxylic acid | 1,6-dihydro-6-oxo-2-(2-n-propoxyphenyl)pyrimidine-5-N-(1H-tetrazol-5-yl)-carboxamide |
| 1,6-dihydro-6-oxo-2-(2-isopropoxyphenyl)pyrimidine-5-carboxylic acid | 1,6-dihydro-6-oxo-2-(2-isopropoxyphenyl)pyrimidine-5-N-(1H-tetrazol-5-yl)-carboxamide |
| 1,6-dihydro-6-oxo-2-(2-n-butoxyphenyl)pyrimidine-5-carboxylic acid | 1,6-dihydro-6-oxo-2-(2-n-butoxyphenyl)pyrimidine-5-N-(1H-tetrazol-5-yl)-carboxamide |
| 1,6-dihydro-6-oxo-2-(2-allyloxyphenyl)pyrimidine-5-carboxylic acid | 1,6-dihydro-6-oxo-2-(2-allyloxyphenyl)pyrimidine-5-N-(1H-tetrazol-5-yl)-carboxamide |
| 1,6-dihydro-6-oxo-2-(2-sec-butoxyphenyl)pyrimidine-5-carboxylic acid | 1,6-dihydro-6-oxo-2-(2-sec-butoxyphenyl)pyrimidine-5-N-(1H-tetrazol-5-yl)-carboxamide |
| 1,6-dihydro-6-oxo-2-(2-t-butoxyphenyl)pyrimidine-5-carboxylic acid | 1,6-dihydro-6-oxo-2-(2-t-butoxyphenyl)pyrimidine-5-N-(1H-tetrazol-5-yl)-carboxamide |
| 1,6-dihydro-6-oxo-2-(2-isobutoxyphenyl)pyrimidine-5-carboxylic acid | 1,6-dihydro-6-oxo-2-(2-isobutoxyphenyl)pyrimidine-5-N-(1H-tetrazol-5-yl)-carboxamide |
| 1,6-dihydro-6-oxo-2-(2,5-dimethoxyphenyl)pyrimidine-5-carboxylic acid | 1,6-dihydro-6-oxo-2-(2,5-dimethoxyphenyl)pyrimidine-5-N-(1H-tetrazol-5-yl)-carboxamide |
| 1,6-dihydro-6-oxo-2-(5-chloro-2-ethoxyphenyl)-pyrimidine-5-carboxylic acid | 1,6-dihydro-6-oxo-2-(5-chloro-2-ethoxyphenyl)-pyrimidine-5-N-(1H-tetrazol-5-yl)carboxamide |
| 1,6-dihydro-6-oxo-2-(5-amino-2-ethoxyphenyl)-pyrimidine-5-carboxylic acid | 1,6-dihydro-6-oxo-2-(5-amino-2-ethoxyphenyl)-pyrimidine-5-N-(1H-tetrazol-5-yl)carboxamide |
| 1,6-dihydro-6-oxo-2-(2-ethoxy-5-methoxyphenyl)-pyrimidine-5-carboxylic acid | 1,6-dihydro-6-oxo-2-(2-ethoxy-5-methoxyphenyl)-pyrimidine-5-N-(1H-tetrazol-5-yl)carboxamide |
| 1,6-dihydro-6-oxo-2-(2-cyclopropylmethoxyphenyl)-pyrimidine-5-carboxylic acid | 1,6-dihydro-6-oxo-2-(2-cyclopropylmethoxyphenyl)-pyrimidine-5-N-(1H-tetrazol-5-yl)carboxamide |
| 1,6-dihydro-6-oxo-2-(5-dimethylamino-2-ethoxy-phenyl)-pyrimidine-5-carboxylic acid | 1,6-dihydro-6-oxo-2-(5-dimethylamino-2-ethoxyphenyl)-pyrimidine-5-N-(1H-tetrazol-5-yl)carboxamide |
| 1,6-dihydro-6-oxo-2-(5-methoxy-2-n-propoxyphenyl)-pyrimidine-5-carboxylic acid | 1,6-dihydro-6-oxo-2-(5-methoxy-2-n-propoxyphenyl)-pyrimidine-5-N-(1H-tetrazol-5-yl)carboxamide |
| 1,6-dihydro-6-oxo-2-(2-methoxyphenyl)pyrimidine-5-carboxylic acid | 1,6-dihydro-6-oxo-2-(2-methoxyphenyl)pyrimidine-5-N-(1H-tetrazol-5-yl)-carboxamide |
| 1,6-dihydro-6-oxo-2-(2-chlorophenyl)pyrimidine-5-carboxylic acid | 1,6-dihydro-6-oxo-2-(2-chlorophenyl)pyrimidine-5-N-(1H-tetrazol-5-yl)-carboxamide |
| 1,6-dihydro-6-oxo-2-(3-methoxyphenyl)pyrimidine-5-carboxylic acid | 1,6-dihydro-6-oxo-2-(3-methoxyphenyl)pyrimidine-5-N-(1H-tetrazol-5-yl)-carboxamide |
| 1,6-dihydro-6-oxo-2-(3-trifluoromethylphenyl)-pyrimidine-5-carboxylic acid | 1,6-dihydro-6-oxo-2-(3-trifluoromethylphenyl)-pyrimidine-5-N-(1H-tetrazol-5-yl)carboxamide |
| 1,6-dihydro-6-oxo-2-(4-methoxyphenyl)pyrimidine-5-carboxylic acid | 1,6-dihydro-6-oxo-2-(4-methoxyphenyl)pyrimidine-5-N-(1H-tetrazol-5-yl)-carboxamide |
| 1,6-dihydro-6-oxo-2-(4-chlorophenyl)pyrimidine-5-carboxylic acid | 1,6-dihydro-6-oxo-2-(4-chlorophenyl)pyrimidine-5-N-(1H-tetrazol-5-yl)-carboxamide |
| 1,6-dihydro-6-oxo-2-(4-trifluoromethylphenyl)-pyrimidine-5-carboxylic acid | 1,6-dihydro-6-oxo-2-(4-trifluoromethylphenyl)-pyrimidine-5-N-(1H-tetrazol-5-yl)carboxamide |
| 1,6-dihydro-6-oxo-2-(5-carbethoxy-2-ethoxyphenyl)-pyrimidine-5-carboxylic acid | 1,6-dihydro-6-oxo-2-(5-carbethoxy-2-ethoxyphenyl)-pyrimidine-5-N-(1H-tetrazol-5-yl)carboxamide |
| 1,6-dihydro-6-oxo-2-(5-nitro-2-ethoxyphenyl)-pyrimidine-5-carboxylic acid | 1,6-dihydro-6-oxo-2-(5-nitro-2-ethoxyphenyl)-pyrimidine-5-N-(1H-tetrazol-5-yl)carboxamide |
| 1,6-dihydro-6-oxo-2-(2,4-dimethoxyphenyl)pyrimidine-5-carboxylic acid | 1,6-dihydro-6-oxo-2-(2,4-dimethoxyphenyl)pyrimidine-5-N-(1H-tetrazol-5-yl)-carboxamide |
| 1,6-dihydro-6-oxo-2-(2-fluorophenyl)pyrimidine-5-carboxylic acid | 1,6-dihydro-6-oxo-2-(2-fluorophenyl)pyrimidine-5-N-(1H-tetrazol-5-yl)-carboxamide |
| 1,6-dihydro-6-oxo-2-(2-benzyloxyphenyl)pyrimidine- | 1,6-dihydro-6-oxo-2-(2-benzyloxyphenyl)pyrimidine- |

-continued

| Table A | Table B |
|---|---|
| 5-carboxylic acid | 5-N-(1H-tetrazol-5-yl)-carboxamide |
| 1,6-dihydro-6-oxo-2-(2-ethylthiophenyl)pyrimidine-5-carboxylic acid | 1,6-dihydro-6-oxo-2-(2-ethylthiophenyl)pyrimidine-5-N-(1H-tetrazol-5-yl)-carboxamide |
| 1,6-dihydro-6-oxo-2-(2-methylthiophenyl)pyrimidine-5-carboxylic acid | 1,6-dihydro-6-oxo-2-(2-methylthiophenyl)pyrimidine-5-N-(1H-tetrazol-5-yl)-carboxamide |
| 1,6-dihydro-6-oxo-2-(2-nitrophenyl)pyrimidine-5-carboxylic acid | 1,6-dihydro-6-oxo-2-(2-nitrophenyl)pyrimidine-5-N-(1H-tetrazol-5-yl)-carboxamide |
| 1,6-dihydro-6-oxo-2-(2-aminophenyl)pyrimidine-5-carboxylic acid | 1,6-dihydro-6-oxo-2-(2-aminophenyl)pyrimidine-5-N-(1H-tetrazol-5-yl)-carboxamide |
| 1,6-dihydro-6-oxo-2-(4-methylphenyl)pyrimidine-5-carboxylic acid | 1,6-dihydro-6-oxo-2-(4-methylphenyl)pyrimidine-5-N-(1H-tetrazol-5-yl)-carboxamide |
| 1,6-dihydro-6-oxo-2-(3-methylphenyl)pyrimidine-5-carboxylic acid | 1,6-dihydro-6-oxo-2-(3-methylphenyl)pyrimidine-5-N-(1H-tetrazol-5-yl)-carboxamide |
| 1,6-dihydro-6-oxo-2-(3-chlorophenyl)pyrimidine-5-carboxylic acid | 1,6-dihydro-6-oxo-2-(3-chlorophenyl)pyrimidine-5-N-(1H-tetrazol-5-yl)-carboxamide |
| 1,6-dihydro-6-oxo-2-(4-hydroxyphenyl)pyrimidine-5-carboxylic acid | 1,6-dihydro-6-oxo-2-(4-hydroxyphenyl)pyrimidine-5-N-(1H-tetrazol-5-yl)-carboxamide |
| 1,6-dihydro-6-oxo-2-(3,4-dimethoxyphenyl)pyrimidine-5-carboxylic acid | 1,6-dihydro-6-oxo-2-(3,4-dimethoxyphenyl)pyrimidine-5-N-(1H-tetrazol-5-yl)-carboxamide |
| 1,6-dihydro-6-oxo-2-(3,4,5-trimethoxyphenyl)pyrimidine-5-carboxylic acid | 1,6-dihydro-6-oxo-2-(3,4,5-trimethoxyphenyl)pyrimidine-5-N-(1H-tetrazol-5-yl)-carboxamide |
| 1,6-dihydro-6-oxo-2-(3-acetamidophenyl)pyrimidine-5-carboxylic acid | 1,6-dihydro-6-oxo-2-(3-acetamidophenyl)pyrimidine-5-N-(1H-tetrazol-5-yl)-carboxamide |
| 1,6-dihydro-6-oxo-2-(2-acetamidophenyl)pyrimidine-5-carboxylic acid | 1,6-dihydro-6-oxo-2-(2-acetamidophenyl)pyrimidine-5-N-(1H-tetrazol-5-yl)-carboxamide |
| 1,6-dihydro-6-oxo-2-(4-dimethylaminophenyl)pyrimidine-5-carboxylic acid | 1,6-dihydro-6-oxo-2-(4-dimethylaminophenyl)pyrimidine-5-N-(1H-tetrazol-5-yl)carboxamide |
| 1,6-dihydro-6-oxo-2-(3,5-dibromophenyl)pyrimidine-5-carboxylic acid | 1,6-dihydro-6-oxo-2-(3,5-dibromophenyl)pyrimidine-5-N-(1H-tetrazol-5-yl)-carboxamide |
| 1,6-dihydro-6-oxo-2-(4-butylthiophenyl)pyrimidine-5-carboxylic acid | 1,6-dihydro-6-oxo-2-(4-butylthiophenyl)pyrimidine-5-N-(1H-tetrazol-5-yl)-carboxamide |
| 1,6-dihydro-6-oxo-2-(4-methylthiophenyl)pyrimidine-5-carboxylic acid | 1,6-dihydro-6-oxo-2-(4-methylthiophenyl)pyrimidine-5-N-(1H-tetrazol-5-yl)-carboxamide |
| 1,6-dihydro-6-oxo-2-(5-amino-2-n-propoxyphenyl)pyrimidine-5-carboxylic acid | 1,6-dihydro-6-oxo-2-(5-amino-2-n-propoxyphenyl)pyrimidine-5-N-(1H-tetrazol-5-yl)carboxamide |
| 1,6-dihydro-6-oxo-2-(5-dimethylamino-2-n-propoxyphenyl)pyrimidine-5-carboxylic acid | 1,6-dihydro-6-oxo-2-(5-dimethylamino-2-n-propoxyphenyl)pyrimidine-5-N-(1H-tetrazol-5-yl)carboxamide |

EXAMPLE 3

Following the general procedure of Example 1, the following compounds may be prepared by use of the appropriate pyrimidine-5-carboxylic acid starting material.

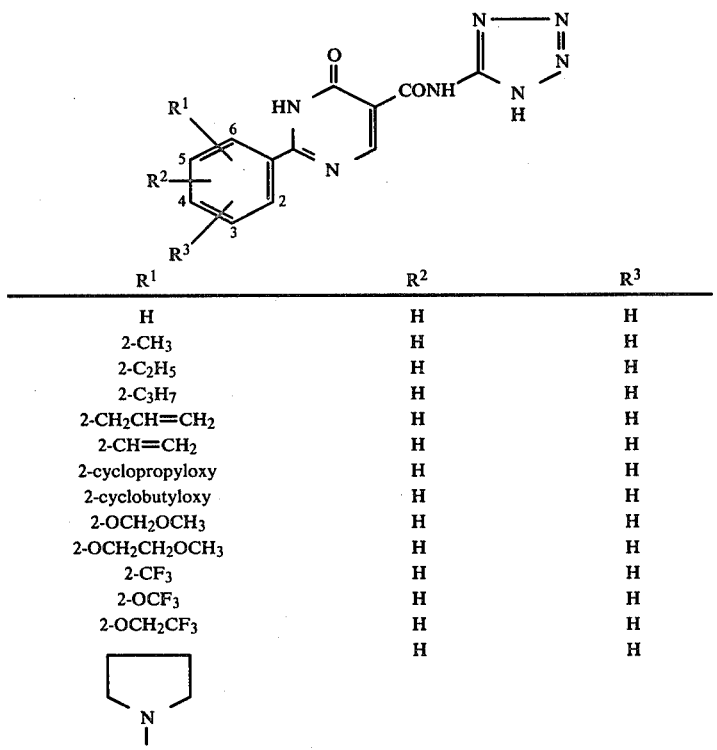

| $R^1$ | $R^2$ | $R^3$ |
|---|---|---|
| H | H | H |
| 2-CH$_3$ | H | H |
| 2-C$_2$H$_5$ | H | H |
| 2-C$_3$H$_7$ | H | H |
| 2-CH$_2$CH=CH$_2$ | H | H |
| 2-CH=CH$_2$ | H | H |
| 2-cyclopropyloxy | H | H |
| 2-cyclobutyloxy | H | H |
| 2-OCH$_2$OCH$_3$ | H | H |
| 2-OCH$_2$CH$_2$OCH$_3$ | H | H |
| 2-CF$_3$ | H | H |
| 2-OCF$_3$ | H | H |
| 2-OCH$_2$CF$_3$ | H | H |
| 2-⟨N⟩ | H | H |

-continued

[Structure: pyrimidinone-carboxamide-tetrazole with phenyl bearing R¹ (6-position), R² (5-position), R³ (4-position), positions 2, 3 on ring]

| R¹ | R² | R³ |
|---|---|---|
| (piperidin-1-yl) | H | H |
| 2-NHCH₃ | H | H |
| 2-NHC₂H₅ | H | H |
| 2-N(CH₃)₂ | H | H |
| 2-COOH | H | H |
| 2-COOCH₃ | H | H |
| 2-COOC₂H₅ | H | H |
| 2-OCH₂CO₂H | H | H |
| 2-OCH₂CO₂CH₃ | H | H |
| 2-OCONHCH₃ | H | H |
| 2—C(O)CH₃ | H | H |
| 2—C(O)—C₂H₅ | H | H |
| 2-O—C(O)—CH₃ | H | H |
| 2-OCH₂CH₂OH | H | H |
| 2-OCH₂—CH(OH)CH₂OH | H | H |
| 2-OCH₂—CH(OH)—CH₂OCH₃ | H | H |
| 2-OCH₂CH₂CH₂OH | H | H |
| 2-OCH=CH₂ | H | H |
| 2-C(CH₃)₃ | H | H |
| 2-OC≡CCH₃ | H | H |
| 2-OCH₂CH₂C≡CH | H | H |
| 2-OC≡CH | H | H |
| 2-F | 5-F | H |
| 2-cyclopropylethoxy | H | H |
| 2-cyclobutylmethoxy | H | H |
| 2-cyclopentyloxy | H | H |
| 2-O-n-C₃H₇ | 5-Cl | H |
| " | 5-F | H |
| " | 5-CH₃ | H |
| " | 5-C₂H₅ | H |
| " | 5-CH₂CH=CH₂ | H |
| " | 5-CH=CH₂ | H |
| " | 5-OC₂H₅ | H |
| " | 5-O-n-C₃H₇ | H |
| " | 5-OCH(CH₃)₂ | H |
| " | 5-OCH₂CH=CH₂ | H |
| " | 5-OCH₂CH₂OCH₃ | H |
| " | 5-CF₃ | H |
| " | 5-OCF₃ | H |
| " | 5-OCH₂CF₃ | H |
| " | 5-OH | H |
| " | 5-SCH₃ | H |
| " | 5-NHCH₃ | H |
| " | 5-N(pyrrolidin-1-yl) | H |

-continued

| R¹ | R² | R³ |
|---|---|---|
| " | 5-N(piperidinyl) | H |
| " | 5-NHC₂H₅ | H |
| " | 5-COOH | H |
| " | 5-CO₂CH₃ | H |
| " | 5-CO₂C₂H₅ | H |
| " | 5-OCH₂CO₂H | H |
| " | 5-OCH₂CO₂CH₃ | H |
| " | 5-O—CONHCH₃ | H |
| " | 5-CCH₃ (C=O) | H |
| " | 5-C—C₂H₅ (C=O) | H |
| " | 5-NHCCH₃ (C=O) | H |
| " | 5-O—CCH₃ (C=O) | H |
| " | 5-OCH₂CH₂OH | H |
| " | 5-OCH₂—CHCH₂OH (OH) | H |
| " | 5-OCH₂—CH—CH₂OCH₃ (OH) | |
| " | 5-OCH₂C₆H₅ | H |
| 2-O—CH(CH₃)₂ | 5-OCH₃ | H |
| " | 5-OC₂H₅ | H |
| " | 5-O-n-C₃H₇ | H |
| " | 5-OCH(CH₃)₂ | H |
| " | 5-OCH₂CH=CH₂ | H |
| " | 5-CF₃ | H |
| 2-OC₂H₅ | 5-OC₂H₅ | H |
| " | 5-O-n-C₃H₇ | H |
| " | 5-OCH(CH₃)₂ | H |
| 2-O-n-C₄H₉ | 5-OC₂H₅ | H |
| " | 5-O-n-C₃H₇ | H |
| " | 5-OCH(CH₃)₂ | H |
| 2-OCH₃ | 4-OCH₃ | 6-OCH₃ |

I claim:
1. A compound having the formula

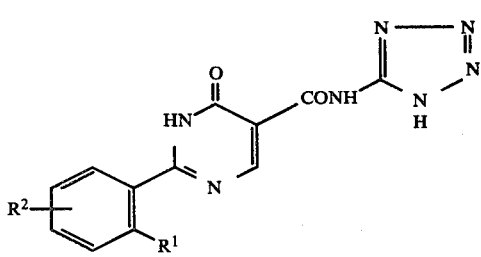

wherein R¹ and R² which may be the same or different are each hydrogen, halogen, (lower)alkyl, (lower)alkoxy, —O—(lower)alkenyl, —O—(lower)alkynyl, —O—(CH₂)$_m$—CH((CH₂)$_n$ in which m is 0 or an integer from 1 to 6 and n is an integer from 2 to 7, CF₃, hydroxy, (lower)alkylthio, amino, (lower)alkylamino, di(-lower)-alkylamino, carboxyl, or —OCH₂C₆H₅, or a pharmaceutically acceptable salt thereof, with the proviso that when R¹ and R² are tertiary alkyl or tertiary alkoxy they are located on non-adjcent positions.

2. A compound of claim 1 wherein R¹ and R² are each independently selected from hydrogen, (lower)alkoxy, —O—(lower)alkenyl, —O—(lower)alkynyl, —O—(CH₂)$_m$—CH((CH₂)$_n$ in which m is 0 or an integer from 1 to 6 and n is an integer from 2 to 7 or —OCH₂C₆H₅.

3. A compound of claim 1 wherein R¹ is (lower)alkoxy, —O—(lower)alkenyl, —O—(lower)alkynyl, —O—(CH₂)$_m$—CH(CH₂)$_n$ in which m is 0 or an integer from 1 to 6 and n is an integer from 2 to 7 or —OCH₂C₆H₅ and R² is hydrogen, (lower)alkoxy, —O—(lower)alkenyl, —O—(lower)alkynyl, —O—(CH$_2$)$_m$—CH(CH$_2$)$_n$ in which m is 0 or an integer from 1 to 6 and n is an integer from 2 to 7, —OCH$_2$C$_6$H$_5$, amino, di(lower)alkylamino or (lower)alkylthio.

4. A compound having the formula

[chemical structure]

wherein R$^1$ and R$^2$ which may be the same or different are each hydrogen, halogen, (lower)alkyl, (lower)alkoxy, —O—(lower)alkenyl, —O—(lower)alkynyl, —O—(CH$_2$)$_m$—CH(CH$_2$)$_n$ in which m is 0 or an integer from 1 to 6 and n is an integer from 2 to 7, CF$_3$, hydroxy, (lower)alkylthio, amino, (lower)alkylamino, di(lower)-alkylamino- carboxyl, or —OCH$_2$C$_6$H$_5$, or a pharmaceutically acceptable salt thereof.

5. A compound of claim 4 wherein R$^1$ and R$^2$ are each independently selected from hydrogen, (lower)alkoxy, —O—(lower)alkenyl, —O—(lower)alkynyl, —O—(CH$_2$)$_m$—CH(CH$_2$)$_n$ in which m is 0 or an integer from 1 to 6 and n is an integer from 2 to 7 or —OCH$_2$C$_6$H$_5$.

6. A compound of claim 4 wherein R$^1$ is (lower)alkoxy, —O—(lower)alkenyl, —O—(lower)alkynyl, —O—(CH$_2$)$_m$—CH(CH$_2$)$_n$ in which m is 0 or an integer from 1 to 6 and n is an integer from 2 to 7 or —OCH$_2$C$_6$H$_5$ and R$^2$ is hydrogen, (lower)alkoxy, —O—(lower)alkenyl, —O—(lower)alkynyl, —O—(CH$_2$)$_m$—CH(CH$_2$)$_n$ in which m is 0 or an integer from 1 to 6 and n is an integer from 2 to 7, —OCH$_2$C$_6$H$_5$, amino di(lower)alkylamino or (lower)alkylthio.

7. A compound of claim 4 wherein R$^1$ is n-propoxy and R$^2$ is methoxy.

8. A compound of claim 4 wherein R$^1$ is n-propoxy and R$^2$ is amino.

9. A compound of claim 4 wherein R$^1$ is n-propoxy and R$^2$ is dimethylamino.

10. A compound having the formula

[chemical structure]

wherein R$^1$ is hydrogen, halogen, (lower)alkyl, (lower)alkenyl, (lower)alkoxy, —O—(lower)alkenyl, —O—(lower)alkynyl, —O—(CH$_2$)$_m$—CH(CH$_2$)$_n$ is which m is 0 or an integer from 1 to 6 and n is an integer from 2 to 7, —OCH$_2$(CH$_2$)$_x$O(CH$_2$)$_y$CH$_3$ in which x is 0 or an integer from 1 to 6 and y is 0 or an integer from 1 to 6, CF$_3$, —OCF$_3$, —OCH$_2$CF$_3$, hydroxy, (lower)alkylthio, amino, nitro, —N(CH$_2$)$_r$ in which r is 4 or 5, (lower)alkylamino, di-(lower)alkylamino, carboxyl, —CO$_2$—(lower)alkyl, —O(CH$_2$)$_u$CO$_2$R$^a$ in which u is an integer from 1 to 6 and R$^a$ is hydrogen or (lower)alkyl, R$^c$—CO— in which R$^c$ is (lower)alkyl, R$^c$—CONH— in which R$^c$ is (lower)alkyl, R$^c$—COO— in which R$^c$ is (lower)-alkyl, $$-O-\overset{O}{\underset{\|}{C}}-NHR^b$$

in which R$^b$ is (lower)alkyl, —(CH$_2$)$_k$OH in which k is an integer from 2 to 6,

—OCH$_2$—CH(OH)—CH$_2$OH, —OCH$_2$—CH(OH)—CH$_2$OCH$_3$ or —OCH$_2$C$_6$H$_5$, or a pharmaceutically acceptable salt thereof.

11. A compound of claim 10 wherein R$^1$ is hydrogen, (lower)-alkoxy, —O—(lower)alkenyl, —O—(lower)alkynyl, —O—(CH$_2$)$_m$—CH(CH$_2$)$_n$ in which m is 0 or an integer from 1 to 6 and n is an integer from 2 to 7, —OCH$_2$C$_6$H$_5$, halogen, CF$_3$, (lower)alkyl, amino, (lower)alkylamino, di(lower)alkylamino, hydroxy, carboxy or (lower) alkylthio.

12. A compound of claim 10 wherein R$^1$ is (lower)alkoxy, —O—(lower)alkenyl, —O—(lower)alkynyl, —O—(CH$_2$)$_m$—CH(CH$_2$)$_n$ in which m is 0 or an integer from 1 to 6 and n is an integer from 2 to 7 or —OCH$_2$C$_6$H$_5$.

13. A compound of claim 10 wherein R$^1$ is (lower)alkoxy.

14. A compound of claim 10 wherein R$^1$ is methoxy, ethoxy, n-propoxy, isopropoxy, n-butoxy, isobutoxy, sec-butoxy or t-butoxy.

15. The compound of claim 10 wherein R$^1$ is methoxy.

16. The compound of claim 10 wheren R$^1$ is ethoxy.

17. The compound of claim 10 wherein R$^1$ is n-propoxy.

18. The compound of claim 10 wherein R$^1$ is isopropoxy.

19. The compound of claim 10 wherein R$^1$ is n-butoxy.

20. The compound of claim 10 wherein R$^1$ is sec-butoxy.

21. The compound of claim 10 wherein R$^1$ is t-butoxy.

22. A compound of claim 10 where R$^1$ is —O—(lower)-alkenyl.

23. The compound of claim 10 wherein R$^1$ is allyloxy.

24. A compound of claim 10 wherein R$^1$ is —O—(lower)-alkynyl.

25. A compound of claim 10 wherein R$^1$ is —O—(CH$_2$)$_m$—CH(CH$_2$)$_n$ in which m is 0 or an integer from 1 to 6 and n is an integer from 2 to 7.

26. The compound of claim 10 wherein R$^1$ is cyclopropylmethoxyl.

27. The compound of claim 10 wherein R$^1$ is —OCH$_2$C$_6$H$_5$.

* * * * *

UNITED STATES PATENT AND TRADEMARK OFFICE
CERTIFICATE OF CORRECTION

PATENT NO. : 4,209,623

DATED : June 24, 1980

INVENTOR(S) : Peter F. Juby

It is certified that error appears in the above-identified patent and that said Letters Patent are hereby corrected as shown below:

Column 23, line 40, insert a comma before "di(lower)alkylamino".

Column 24, line 14, "$-(CH_2)_k OH$" should read -- $-O(CH_2)_k OH$ --.

Signed and Sealed this

Thirtieth Day of September 198

[SEAL]

Attest:

SIDNEY A. DIAMOND

Attesting Officer

Commissioner of Patents and Trademar